(12) United States Patent
Hofmann et al.

(10) Patent No.: US 7,699,792 B2
(45) Date of Patent: Apr. 20, 2010

(54) CATHETER GUIDE WIRE ESPECIALLY FOR PERCUTANEOUS TRANSLUMINAL CORONARY ANGIOPLASTY

(75) Inventors: Eugen Hofmann, Zürich (CH); Christoph Wintsch, Brütten (CH)

(73) Assignee: Biotronik VI Patent AG, Baar (CH)

( * ) Notice: Subject to any disclaimer, the term of this patent is extended or adjusted under 35 U.S.C. 154(b) by 795 days.

(21) Appl. No.: 11/125,309

(22) Filed: May 10, 2005

(65) Prior Publication Data
US 2005/0267385 A1    Dec. 1, 2005

(30) Foreign Application Priority Data
May 10, 2004    (DE) .................. 10 2004 023 642

(51) Int. Cl.
*A61B 5/00*    (2006.01)
(52) U.S. Cl. .................................... 600/585
(58) Field of Classification Search ............ 600/585, 600/431, 434, 435; 604/163.13
See application file for complete search history.

(56) References Cited

U.S. PATENT DOCUMENTS

| | | | |
|---|---|---|---|
| 4,685,904 A | | 8/1987 | Krebs |
| 5,209,730 A | | 5/1993 | Sullivan et al. |
| 5,406,960 A | * | 4/1995 | Corso, Jr. .................. 600/585 |
| 5,465,733 A | * | 11/1995 | Hinohara et al. ............ 600/585 |
| 5,479,938 A | | 1/1996 | Weier et al. |
| 5,957,903 A | * | 9/1999 | Mirzaee et al. .............. 604/524 |
| 6,620,114 B2 | * | 9/2003 | Vrba et al. ................... 600/585 |
| 2002/0042582 A1 | | 4/2002 | Vrba et al. |
| 2003/0088195 A1 | * | 5/2003 | Vardi et al. .................. 600/585 |
| 2003/0100848 A1 | | 5/2003 | Gosiengfiao et al. |

FOREIGN PATENT DOCUMENTS

| | | |
|---|---|---|
| DE | 306891 | 1/1916 |
| DE | 7925924 | 5/1980 |
| DE | 3508013 A1 | 2/1986 |
| DE | 9014195.4 U1 | 4/1991 |
| DE | 69027327 T2 | 1/1997 |
| DE | 19622184 A1 | 12/1997 |
| DE | 10192161 T1 | 6/2002 |
| DE | 20213949 U1 | 2/2003 |
| DE | 102 43 261 A1 | 3/2004 |
| DE | 20315872 | 3/2004 |
| DE | 20218083 U1 | 5/2004 |
| DE | 10256120 A1 | 6/2004 |
| EP | 377453 A1 * | 7/1990 |
| EP | 0486720 A1 | 5/1992 |
| EP | 0749334 B1 | 6/2000 |
| WO | WO 81/00676 | 3/1981 |
| WO | WO 95/24237 | 9/1995 |
| WO | WO 01/191842 | 12/2001 |
| WO | WO 2004/045682 A2 | 5/2004 |

* cited by examiner

*Primary Examiner*—Max Hindenburg
*Assistant Examiner*—Michael C Stout
(74) *Attorney, Agent, or Firm*—Browdy and Neimark, PLLC

(57) ABSTRACT

A catheter guide wire, especially for percutaneous transluminal coronary angioplasty, comprises an elongated wire shaft of a flexible material having a proximal and a distal end and disposed on the wire shaft at least one radiopaque, sleeve-like marker adjacent to the distal end. The at least one marker is disposed on a core section of the wire shaft, said core section being widened in its diameter relative to the diameter of the adjoining shaft sections.

12 Claims, 1 Drawing Sheet

CATHETER GUIDE WIRE ESPECIALLY FOR PERCUTANEOUS TRANSLUMINAL CORONARY ANGIOPLASTY

FIELD OF THE INVENTION

The invention relates to a catheter guide wire, especially for percutaneous transluminal coronary angioplasty (PTCA).

BACKGROUND OF THE INVENTION

Catheter guide wires of a known type have an elongated wire shaft of a flexible material with a proximal and a distal end. In the distal end area, one or more radiopaque, sleeve-like markers are disposed on the wire shaft, which have essentially two functions. On one hand, the position of the guide wire tip must be easily visible on an x-ray monitor—for example by means of an elongated marker coil directly at the distal end of the guide wire—while the catheter is being applied. On the other hand, a length measurement of a stenosis to be treated can be performed on the X-ray monitor, for example, with the aid of multiple markers that are equidistantly spaced adjacent to the distal end.

Guide wires of this type are known in their fundamental design from a multitude of printed publications. U.S. Pat. No. 5,209,730 A, for example, shows a catheter guide wire that has an elongated wire shaft of a flexible material, namely high-strength stainless steel. On it, radiopaque markers are disposed adjacent to the distal end, which are formed by coiled spring elements—so-called "coils"—and which serve—as mentioned above—for measuring the length of stenoses.

U.S. Pat. No. 5,479,938 reveals a similar catheter guide wire on whose shaft radiopaque markers in the form of metal sleeves—also for measuring the length of stenoses—are disposed spaced progressively further apart as their distance from the distal end increases. They may be beveled at their front edges facing in the longitudinal direction of the wire.

Catheter guide wires of this type pose the problem that the wire, especially at its distal end, needs to be as flexible as possible on one hand in order to ensure the most atraumatic insertion of the wire into coronary vessels, and in the process a smooth passage through narrow points and bends in the vasculature being targeted; on the other hand, the markers that are used to identify the guide wire in the case of an X-ray monitoring during the performance of a PTCA, require a certain material volume in order to keep the achievable contrast in the X-ray image at a suitable level. The markers based on a helically wound wire coil that were mentioned at the beginning thus need be mounted on the largest possible winding core, which is diametrically opposed to the demand for the thinnest possible diameter of the wire shaft.

To solve this problem, the invention proposes that the marker or markers are disposed in each case on a core section that is widened in its diameter relative to the adjoining shaft sections of the wire shaft. In other words, a positioning surface that permits a larger diameter of the marker sleeve relative to the remaining wire shaft is provided, only at the locations where the marker is to be located. To maintain the flexibility of the guide wire, the sections that are located between the markers are implemented thinner. The thickened core sections do not cause any significant deterioration of the bending behavior of such guide wires since the flexibility in the regions of the markers is already restricted by this additional component. Additionally, the thickened core section renders the coils easier to solder and center.

According to preferred embodiments of the invention, the core sections transition on both sides in ramp-like annular shoulders in each case into the adjoining shaft section. This prevents sharp inner corners and edges that are difficult to manage from a production aspect given the small dimensions of such guide wires. This is true especially for the processing steps of grinding and polishing the wire. Sharp inner corners would eventually lead to an increased susceptibility of the wire shaft to notch breakage.

According to an additional preferred embodiment, provision is made for the marker, which is implemented as a wire coil, to be secured in each case on the core section by means of a solder bed. The solder bed tapers off at its two ends in a frusto-conical ramp in each case toward the adjoining shaft section and is adapted in this manner to the conical annular shoulder of the core sections. In this respect no interfering edges result on the product, especially after the grinding and polishing of such a guide wire with marker, which could cause injuries to the vessel wall—so-called "dissections"—while the wire is being inserted.

Additional preferred embodiments relate to the dimension ratios of the wire shaft and multiple markers. Of advantage in this case is especially the somewhat smaller outside diameter of the markers in comparison with the distal marker coils that customarily exist on such catheter wires.

This prevents a jolt-like onset of friction when the guide wire is shifted relative to the PTCA catheter. Additional characteristics, advantages and details of the invention will become apparent from the following description, in which an example embodiment will be explained in more detail based on the appended drawings.

DESCRIPTION OF THE PREFERRED EMBODIMENT

Figure 1:
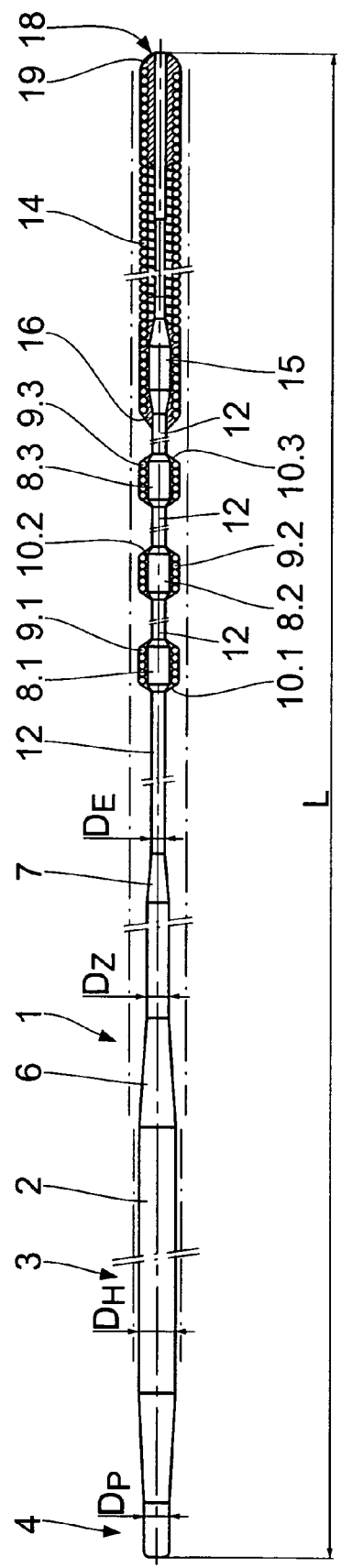
FIG. 1 shows a longitudinal axis section of a catheter guide wire.
Figure 2:
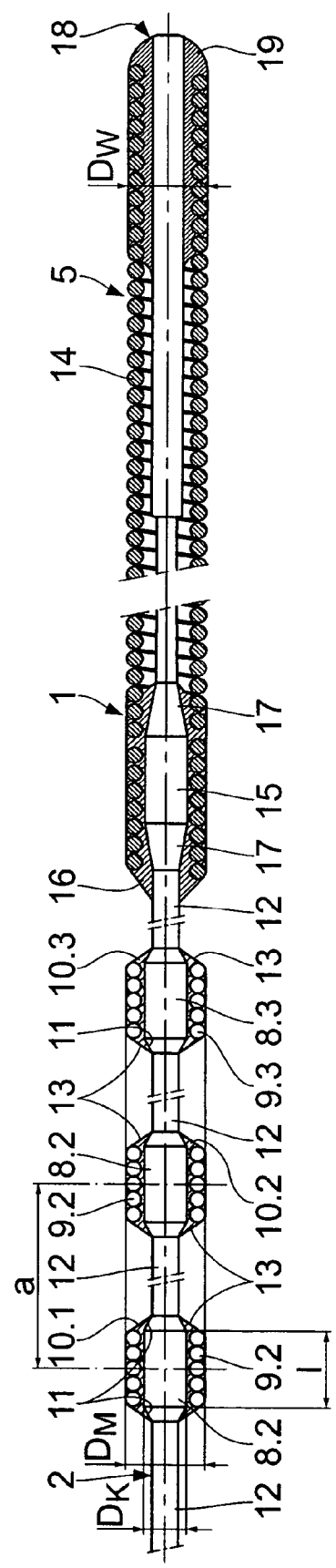
FIG. 2 shows an enlarged longitudinal axis section of the distal end portion of the guide wire according to FIG. 1.

As is apparent from FIG. 1, the guide wire, which has been marked in its entirety with 1, incorporates an elongated wire shaft 2 of medical-grade stainless steel. Shaft sections of varying diameters are provided over its total length L of, for example, 1750 mm. The wire shaft 2 thus has at its proximal end 3, for example, a conically narrowing end section, whose outside diameter $D_P$ of, for example 0.223 mm, is significantly smaller than the main diameter $D_H$ of the wire shaft 2 of 0.36 mm. The conically narrowing proximal end 3 of the wire shaft 2 serves to attach a wire extension.

In the distal end zone, whose length may be altogether approximately 300 mm, which is located adjacent to the distal end 5 of the guide wire 5, the wire shaft 2 is reduced in its thickness from its main diameter $D_H$ over conical ramps 6, 7 to an intermediate diameter $D_Z$ of approximately 0.2 mm and to a final diameter $D_E$ of approximately 0.12 mm. In the process, however, core sections 8.1, 8.2, 8.3, with a widened diameter $D_K$ are formed during the grinding process at three locations that are spaced apart by a center distance α of approximately 10 mm, which serve as support surfaces for a radiopaque marker 9.1, 9.2, 9.3, in each case. These markers 9 have a length l of approximately 1 mm and are formed in each case by a wire coil of a platinum-iridium alloy. Other materials for X-ray marker coils of this type may be gold, tantalum or tungsten, for example. The outside diameter $D_M$ of the markers 9.1, 9.2, 9.3 corresponds to the diameter $D_H$ of the wire shaft 2.

Each of the three wire coils 9.1, 9.2, 9.3, is secured by means of a solder bed 10.1, 10.2, 10.3 on the respective core section 8.1, 8.2, 8.3. The core sections 8.1, 8.2, 8.3 transition via conically implemented, ramp-like annular shoulders 11 in each case into the adjoining shaft sections 12. Likewise, the solder beds 10.1, 10.2, 10.3 are ground and polished in such a way that they transition with a frusto-conical ramp 13 toward the respective shaft section 12. The annular shoulder 11 of the core sections 8.1, 8.2, 8.3 and the conical ramps 13 of the solder beds 10.1, 10.2, 10.3 are flush with one another in the longitudinal axis direction.

Lastly, at the distal end 5, a marker coil 14 is provided that extends over approximately 28 mm and that is connected at its proximal end to a shaft widening 15 with the aid of a solder bed 16 that extends over multiple coil helixes. Said solder bed 16 is implemented in the proximal direction toward the thin shaft section 12 also as a conical ramp 17. The shaft widening 15 with the solder bed 16 for securing the marker coil 14 serves as a transfer means for the reliable introduction of a torque into the distal end of the guide wire 1. At the tip 18 of the guide wire 1, the marker coil 14 is permanently connected with the aid of an additional solder bed 19 to the wire shaft 2, which is flattened in that area.

The outside diameter $D_M$ of the markers 9.1 is identical to or slightly smaller than the outside diameter $D_W$ of the marker coils 14. The entire guide wire 1 is—by the way—coated extremely thin in a known manner with friction-reducing coatings that alternate from wire section to wire section, for example on PTFE or silicon basis, or with a hydrophilic material.

What is claimed is:

1. A catheter guide wire, comprising
   an elongated wire shaft (2) of a flexible material having a proximal end and a distal end (3, 5),
   at least one radiopaque marker (9) disposed on the wire shaft (2) adjacent to the distal end (3), wherein: said at least one marker (9) comprises a wire coil; said wire shaft comprises a core section (8) having an outer surface on which said wire coil is disposed; said wire coil is disposed entirely on said core section (8) of the wire shaft (2); said wire shaft has shaft sections (12) adjoining said core section; said core section (8) has a first diameter ($D_K$); each of said shaft sections (12) adjoining said core section (8) has a second diameter ($D_E$) that is smaller than said first diameter; two of said shaft sections (12) are disposed at respective opposite sides of said core section (8); said core section (8) has a length (l) that is substantially equal to the length (l) of said wire coil (9); and said shaft sections (12) form constricted, flexible catheter guide wire portions at each side of said at least one marker (9).

2. A catheter guide wire according to claim 1, wherein said core section (8) changes over at each side thereof to a respective adjoining shaft section (12) via a conically implemented, ramp-type annular shoulder (11).

3. A catheter guide wire according to claim 1, wherein said core section (8) is formed for said at least one marker (9) by grinding down the wire shaft (2) in a region around both sides of said core section (8).

4. A catheter guide wire according to claim 1, wherein said wire coil is secured on said core section (8) by means of a solder bed (10), which tapers off at each side of said core section (8) in a frusto-conical ramp (13) toward a respective adjoining, shaft section (12).

5. A catheter guide wire according to claim 4, wherein said core section (8) changes over at each side thereof to a respective adjoining shaft section (12) via a conically implemented, ramp-type annular shoulder (11), and said annular shoulder (11) of said core section (8) and a conical ramp (13) of a respective solder bed (10) are flush with one another in a longitudinal axis direction.

6. A catheter guide wire according to claim 1, wherein said at least one marker comprises three said markers disposed adjacent to the distal end (5) of the wire shaft (2) and said three markers are disposed at a distance (a) from one another, and said catheter guide wire further comprises an elongated marker coil (14) at said distal end.

7. A catheter guide wire according to claim 6, wherein the ratio of the length (l) of each marker (9) to the spacing (a) between them is approximately 1:10.

8. A catheter guide wire according to claim 1, wherein an outside diameter ($D_M$) of said at least one marker (9) is slightly smaller than an outside diameter ($D_w$) of an elongated marker coil (14) at the distal end (5) of the wire shaft (2).

9. A catheter guide wire according to claim 5, wherein the surface of the guide wire (1) with said wire shaft (2), and the surface of the at least one marker (9) and of the solder bed (10) are smoothed.

10. A catheter guide wire according to claim 1, comprising a friction-reducing coating on the guide wire (1).

11. A catheter guide wire according to claim 1, wherein said wire coil is made of a first, radiopaque, material and said wire shaft, including said core section, is made of a second material different from said first material.

12. A catheter guide wire according to claim 1, wherein said wire coil is disposed exclusively on said core section.

* * * * *